US011419903B2

(12) United States Patent
Kovarik

(10) Patent No.: US 11,419,903 B2
(45) Date of Patent: *Aug. 23, 2022

(54) METHOD AND SYSTEM FOR REDUCING THE LIKELIHOOD OF OSTEOPOROSIS

(71) Applicant: Joseph E. Kovarik, Englewood, CO (US)

(72) Inventor: Joseph E. Kovarik, Englewood, CO (US)

(73) Assignee: SEED HEALTH, INC., Venice, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/023,736

(22) Filed: Sep. 17, 2020

(65) Prior Publication Data

US 2021/0000883 A1 Jan. 7, 2021

Related U.S. Application Data

(63) Continuation-in-part of application No. 17/011,175, filed on Sep. 3, 2020, now Pat. No. 11,273,187, which is a continuation-in-part of application No. 16/722,117, filed on Dec. 20, 2019, now Pat. No. 10,842,834, which is a continuation-in-part of application No. 16/229,252, filed on Dec. 21, 2018, now Pat. No. 10,512,661, which is a continuation-in-part of application No. 15/392,173, filed on Dec. 28, 2016, now Pat. No. 10,245,288, application No. 17/023,736, which is a continuation-in-part of application No. 16/917,096, filed on Jun. 30, 2020, now Pat. No. 10,940,169, which is a continuation-in-part of application No. 16/782,364, filed on Feb. 5, 2020, now Pat. No. 10,835,560, which is a continuation-in-part of application No. 16/423,375, filed on May 28, 2019, now Pat. No. 10,555,976, which is a continuation of application No. 16/160,336, filed on Oct. 15, 2018, now Pat. No. 10,314,866, which is a continuation of application No. 15/403,823, filed on Jan. 11, 2017, now Pat. No. 10,111,913, application No. 17/023,736, which is a continuation-in-part of application No. 15/270,034, filed on Sep. 20, 2016, now Pat. No. 9,750,802, which is a continuation-in-part of application No. 14/954,074, filed on Nov. 30, 2015, now Pat. No. 9,457,077, application No. 17/023,736, which is a continuation-in-part of application No. 16/426,346, filed on May 30, 2019, now Pat. No. 10,716,815, which is a continuation of application No. 15/639,767, filed on Jun. 30, 2017, now Pat. No. 10,314,865, which is a continuation-in-part of application No. 15/437,976, filed on Feb. 21, 2017, now Pat. No. 9,730,967, which is a continuation-in-part of application No. 15/228,454, filed on Aug. 4, 2016, now Pat. No. 9,585,920, which is a continuation-in-part of application No. 14/954,074, filed on Nov. 30, 2015, now Pat. No. 9,457,077, application No. 17/023,736, which is a continuation-in-part of application No. 16/776,861, filed on Jan. 30, 2020, now Pat. No. 10,864,109, which is a continuation of application No. 16/142,171, filed on Sep. 26, 2018, now Pat. No. 10,548,761, which is a continuation-in-part of application No. 15/395,419, filed on Dec. 30, 2016, now Pat. No. 10,086,018, application No. 17/023,736, which is a continuation-in-part of (Continued)

(51) Int. Cl.
| | |
|---|---|
| A61K 35/74 | (2015.01) |
| A61K 31/715 | (2006.01) |
| A61K 38/17 | (2006.01) |
| A61K 31/58 | (2006.01) |
| A61K 35/00 | (2006.01) |

(52) U.S. Cl.
CPC ............. *A61K 35/74* (2013.01); *A61K 31/58* (2013.01); *A61K 31/715* (2013.01); *A61K 38/1709* (2013.01); *A61K 38/1758* (2013.01); *A61K 2035/11* (2013.01)

(58) Field of Classification Search
None
See application file for complete search history.

(56) References Cited

U.S. PATENT DOCUMENTS

| | | |
|---|---|---|
| 3,178,341 A | 4/1965 | Hamill et al. |
| 3,832,460 A | 8/1974 | Kosti |

(Continued)

FOREIGN PATENT DOCUMENTS

| | | |
|---|---|---|
| WO | PCT/US2008/080362 | 4/2009 |
| WO | WO 2011/020780 | 2/2011 |

(Continued)

OTHER PUBLICATIONS

Malaguarnera et al. (Dig Dis Sci, 57:545-553, 2012).

*Primary Examiner* — Brian Gangle
(74) *Attorney, Agent, or Firm* — Sheridan Ross P.C.

(57) ABSTRACT

Various embodiments of the present invention are directed to the field of treating and preventing osteoporosis, with particular embodiments directed to a method of ameliorating, treating, or preventing osteoporosis in a human subject employing tomatidine, xylitol, rapamycin, etc., as well as modifying an individual's microbiome to reduce the likelihood of osteoporosis.

19 Claims, 3 Drawing Sheets

Related U.S. Application Data application No. 16/904,056, filed on Jun. 17, 2020, which is a continuation-in-part of application No. 15/983,250, filed on May 18, 2018, now Pat. No. 10,687,975, which is a continuation-in-part of application No. 15/384,716, filed on Dec. 20, 2016, now Pat. No. 9,987,224, application No. 17/023,736, which is a continuation-in-part of application No. 15/270,034, filed on Sep. 20, 2016, now Pat. No. 9,750,802, which is a continuation-in-part of application No. 14/954,074, filed on Nov. 30, 2015, now Pat. No. 9,457,077.

(60) Provisional application No. 62/275,341, filed on Jan. 6, 2016, provisional application No. 62/296,186, filed on Feb. 17, 2016, provisional application No. 62/274,550, filed on Jan. 4, 2016, provisional application No. 62/387,405, filed on Dec. 24, 2015.

(56) References Cited

U.S. PATENT DOCUMENTS

| | | |
|---|---|---|
| 4,136,162 A | 1/1979 | Fuchs et al. |
| 4,568,639 A | 2/1986 | Lew |
| 4,687,841 A | 8/1987 | Spilburg et al. |
| 4,720,486 A | 1/1988 | Spilburg et al. |
| 4,995,555 A | 2/1991 | Woodruff |
| 5,002,970 A | 3/1991 | Eby, III |
| 5,277,877 A | 1/1994 | Jeffrey et al. |
| 5,614,501 A | 3/1997 | Richards |
| 5,719,196 A | 2/1998 | Uhari |
| 6,054,143 A | 4/2000 | Jones |
| 6,139,861 A | 10/2000 | Friedman |
| 6,210,699 B1 | 4/2001 | Acharya |
| 6,287,610 B1 | 9/2001 | Bowling et al. |
| 6,569,474 B2 | 5/2003 | Clayton et al. |
| 6,599,883 B1 | 7/2003 | Romeo |
| 6,722,577 B2 | 4/2004 | Dobyns, III |
| 6,919,373 B1 | 7/2005 | Lam et al. |
| 7,087,249 B2 | 8/2006 | Burrell |
| 7,267,975 B2 | 9/2007 | Strobel et al. |
| 7,353,194 B1 | 4/2008 | Kerker et al. |
| 7,540,432 B2 | 6/2009 | Majerowski et al. |
| 7,820,420 B2 | 10/2010 | Whitlock |
| 7,862,808 B2 | 1/2011 | Isolauri et al. |
| 7,901,925 B2 | 3/2011 | Bojrab |
| 8,034,606 B2 | 10/2011 | Park et al. |
| 8,197,872 B2 | 6/2012 | Mills et al. |
| 8,349,313 B2 | 1/2013 | Smith et al. |
| 8,420,074 B2 | 4/2013 | Rehberger et al. |
| 8,454,729 B2 | 6/2013 | Mittelmark et al. |
| 8,481,299 B2 | 7/2013 | Gueniche |
| 8,496,914 B2 | 7/2013 | Bonfiglio |
| 8,585,588 B2 | 11/2013 | Kovarik et al. |
| 8,685,389 B2 | 4/2014 | Baur |
| 8,701,671 B2 | 4/2014 | Kovarik |
| 8,716,327 B2 | 5/2014 | Zhao |
| 8,758,764 B2 | 6/2014 | Masignani et al. |
| 8,815,538 B2 | 8/2014 | Lanzalaco et al. |
| 8,865,211 B2 | 10/2014 | Tzannis |
| 8,945,839 B2 | 2/2015 | Zhang |
| 8,951,775 B2 | 2/2015 | Castiel |
| 8,999,372 B2 | 4/2015 | Davidson |
| 9,011,834 B1 | 4/2015 | McKenzie et al. |
| 9,017,718 B2 | 4/2015 | Tan |
| 9,028,841 B2 | 5/2015 | Henn et al. |
| 9,131,884 B2 | 9/2015 | Holmes |
| 9,234,204 B2 | 1/2016 | Qvit-Raz et al. |
| 9,288,981 B2 | 3/2016 | Gandhi et al. |
| 10,245,288 B2 | 4/2019 | Kovarik |
| 10,512,661 B2 | 12/2019 | Kovarik |
| 10,683,323 B2 | 6/2020 | Krakash et al. |
| 10,760,075 B2 | 9/2020 | Sommer et al. |
| 2003/0031737 A1 | 2/2003 | Rosenbloom |
| 2003/0206995 A1 | 11/2003 | Bowling et al. |
| 2004/0053352 A1 | 3/2004 | Ouyang et al. |
| 2004/0096569 A1 | 5/2004 | Barkalow et al. |
| 2004/0115223 A1 | 6/2004 | Follansbee |
| 2004/0120991 A1 | 6/2004 | Schobel |
| 2004/0142463 A1 | 7/2004 | Walker et al. |
| 2004/0166501 A1 | 8/2004 | Azimzai et al. |
| 2004/0170617 A1 | 9/2004 | Finegold |
| 2004/0228804 A1 | 11/2004 | Jones et al. |
| 2005/0118655 A1 | 6/2005 | Weinstock et al. |
| 2005/0196358 A1 | 9/2005 | Georglades et al. |
| 2006/0035008 A1 | 2/2006 | Virgalli et al. |
| 2006/0252087 A1 | 11/2006 | Tang et al. |
| 2007/0054008 A1 | 3/2007 | Clayton et al. |
| 2007/0057086 A1 | 3/2007 | Van Kippersluis |
| 2007/0059718 A1 | 3/2007 | Toner et al. |
| 2007/0059774 A1 | 3/2007 | Grisham et al. |
| 2007/0063026 A1 | 3/2007 | Mamaropolos et al. |
| 2007/0087020 A1 | 4/2007 | O'Connor |
| 2007/0207955 A1 | 9/2007 | Tanihara et al. |
| 2007/0218114 A1 | 9/2007 | Sorousch |
| 2007/0231923 A1 | 10/2007 | Cumberland et al. |
| 2008/0112983 A1 | 5/2008 | Bufe et al. |
| 2008/0267933 A1 | 10/2008 | Ohlson et al. |
| 2008/0305089 A1 | 12/2008 | Bufe et al. |
| 2009/0196907 A1 | 8/2009 | Bunick |
| 2009/0196908 A1 | 8/2009 | Lee |
| 2009/0205083 A1 | 8/2009 | Gupta et al. |
| 2010/0029832 A1 | 2/2010 | Pinnavaia et al. |
| 2010/0260720 A1 | 10/2010 | Sprenger |
| 2010/0285098 A1 | 11/2010 | Haley |
| 2011/0142942 A1 | 6/2011 | Gardner et al. |
| 2011/0217368 A1 | 9/2011 | Prakash et al. |
| 2012/0027786 A1 | 2/2012 | Gupta |
| 2012/0029832 A1 | 2/2012 | Dodgson |
| 2012/0039806 A1 | 2/2012 | Lahoud et al. |
| 2012/0058094 A1 | 3/2012 | Blasser et al. |
| 2012/0128597 A1 | 5/2012 | Peters et al. |
| 2012/0142548 A1 | 6/2012 | Corsi et al. |
| 2012/0276143 A1 | 11/2012 | O'Mahony et al. |
| 2012/0276525 A1 | 11/2012 | Kovarik et al. |
| 2013/0059815 A1 | 3/2013 | Fournell et al. |
| 2013/0157876 A1 | 6/2013 | Lynch et al. |
| 2013/0259834 A1 | 10/2013 | Klaenhammer |
| 2013/0315869 A1 | 11/2013 | Qimron et al. |
| 2013/0323025 A1 | 12/2013 | Crawford et al. |
| 2013/0323100 A1 | 12/2013 | Poulton et al. |
| 2013/0326645 A1 | 12/2013 | Cost et al. |
| 2013/0330215 A1 | 12/2013 | Li |
| 2014/0044677 A1 | 2/2014 | Qvit-Raz et al. |
| 2014/0045744 A1 | 2/2014 | Gordon |
| 2014/0065209 A1 | 3/2014 | Putaala et al. |
| 2014/0065218 A1 | 3/2014 | Lang et al. |
| 2014/0066817 A1 | 3/2014 | Kovarik et al. |
| 2014/0068797 A1 | 3/2014 | Doudna et al. |
| 2014/0154290 A1 | 6/2014 | Peters et al. |
| 2014/0199266 A1 | 7/2014 | Park |
| 2014/0238411 A1 | 8/2014 | Kovarik |
| 2014/0255351 A1 | 9/2014 | Berstad et al. |
| 2014/0271867 A1 | 9/2014 | Myers |
| 2014/0333003 A1 | 11/2014 | Allen |
| 2014/0349405 A1 | 11/2014 | Sontheimer et al. |
| 2014/0356460 A1 | 12/2014 | Lutin |
| 2014/0363441 A1 | 12/2014 | Grandea, III et al. |
| 2014/0377278 A1 | 12/2014 | Elinav et al. |
| 2015/0017227 A1 | 1/2015 | Kim |
| 2015/0064138 A1 | 3/2015 | Lu et al. |
| 2015/0071957 A1 | 3/2015 | Kelly |
| 2015/0086581 A1 | 3/2015 | Li et al. |
| 2015/0093473 A1 | 4/2015 | Barrangou |
| 2015/0132263 A1 | 5/2015 | Liu et al. |
| 2015/0150792 A1 | 6/2015 | Klingman |
| 2015/0166641 A1 | 6/2015 | Goodman |
| 2015/0190435 A1 | 7/2015 | Henn et al. |
| 2015/0216917 A1 | 8/2015 | Jones |
| 2015/0252358 A1 | 9/2015 | Maeder |
| 2015/0329555 A1 | 11/2015 | Liras |
| 2015/0329875 A1 | 11/2015 | Gregory |
| 2015/0352023 A1 | 12/2015 | Berg |

(56) References Cited

U.S. PATENT DOCUMENTS

| | | |
|---|---|---|
| 2015/0353901 A1 | 12/2015 | Liu |
| 2015/0361436 A1 | 12/2015 | Hitchcock |
| 2015/0374607 A1 | 12/2015 | Lanzalaco et al. |
| 2016/0008412 A1 | 1/2016 | Putaala et al. |
| 2016/0040216 A1 | 2/2016 | Wilder |
| 2016/0089315 A1 | 3/2016 | Kleinberg et al. |
| 2016/0089405 A1 | 3/2016 | Lue |
| 2016/0151427 A1 | 6/2016 | Whitlock et al. |
| 2016/0168594 A1 | 6/2016 | Zhang et al. |
| 2016/0199424 A1 | 7/2016 | Berry et al. |
| 2016/0206564 A1 | 7/2016 | Trachtman |
| 2016/0213702 A1 | 7/2016 | Von Maltzahn et al. |
| 2016/0243132 A1 | 8/2016 | Adams et al. |
| 2016/0271189 A1 | 9/2016 | Cutcliffe |
| 2016/0314281 A1 | 10/2016 | Apte |
| 2017/0014341 A1 | 1/2017 | Armer et al. |
| 2017/0312232 A1 | 11/2017 | Vitetta et al. |
| 2018/0000878 A1 | 1/2018 | Goodman et al. |
| 2018/0140698 A1 | 5/2018 | Clube |
| 2018/0207165 A1 | 7/2018 | Harmsen et al. |
| 2018/0296582 A1 | 10/2018 | Von Maltzahn et al. |
| 2018/0312851 A1 | 11/2018 | Falb et al. |
| 2018/0326008 A1 | 11/2018 | Schreiber et al. |
| 2019/0262298 A1 | 8/2019 | Kanthasamy et al. |
| 2019/0390284 A1 | 12/2019 | Kim |
| 2020/0032224 A1 | 1/2020 | Schaefer et al. |
| 2020/0188454 A1 | 6/2020 | Slykerman |

FOREIGN PATENT DOCUMENTS

| | | | |
|---|---|---|---|
| WO | WO 2013/026000 | 2/2013 | |
| WO | WO 2011/029701 | 5/2013 | |
| WO | WO 2013/107750 | 7/2013 | |
| WO | PCT/US2014/036849 | 5/2014 | |
| WO | WO-2016070151 A1 * | 5/2016 | ............... A61K 9/48 |
| WO | WO 2017/211753 | 12/2017 | |

\* cited by examiner

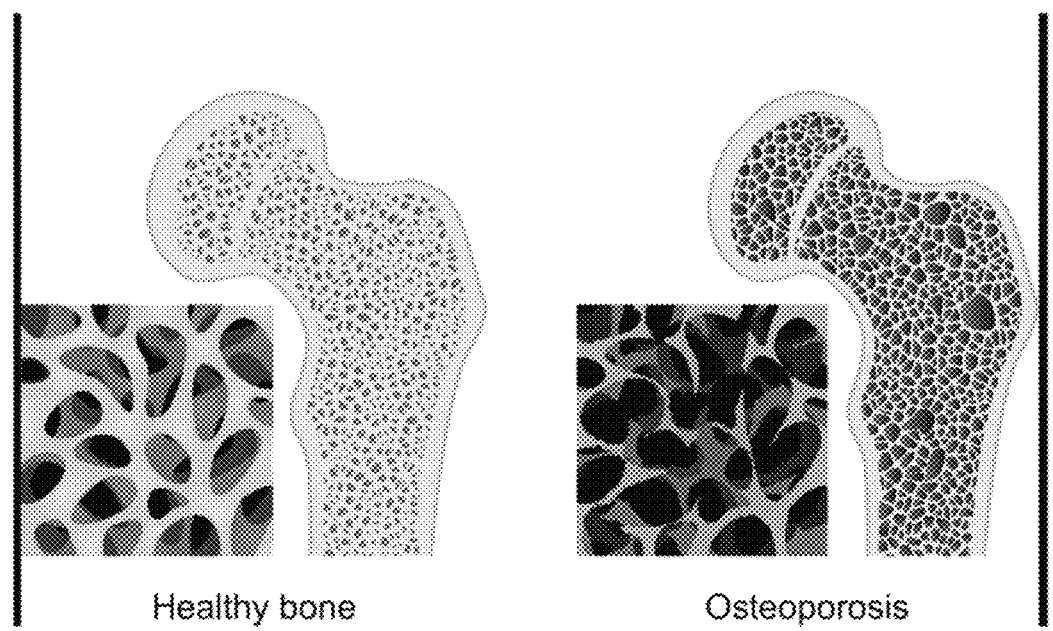
Figure 1
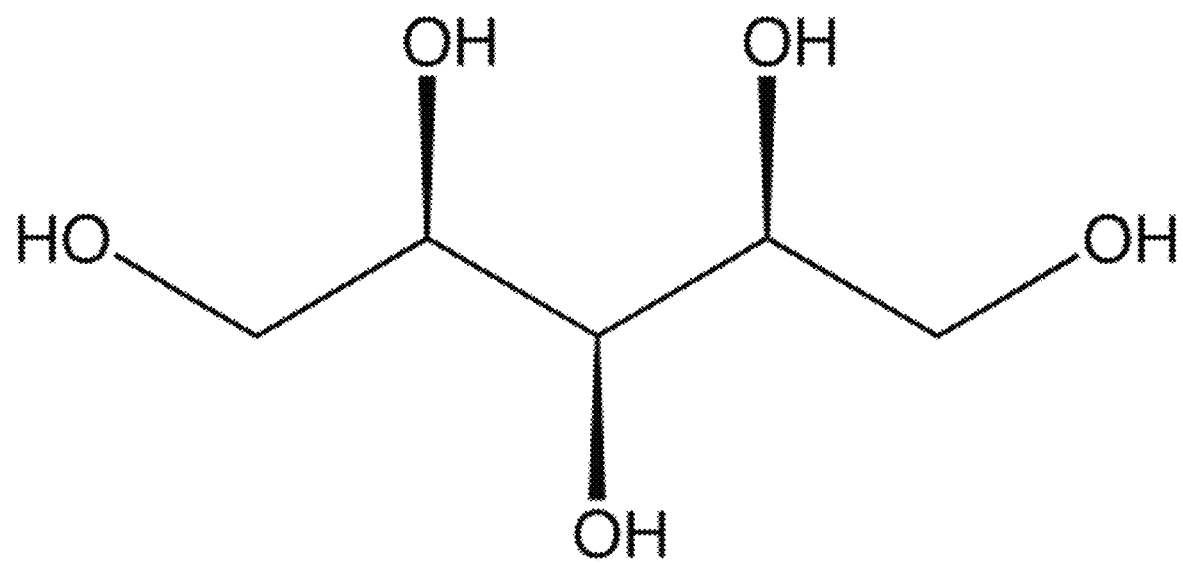
Fig. 2 - Xylitol

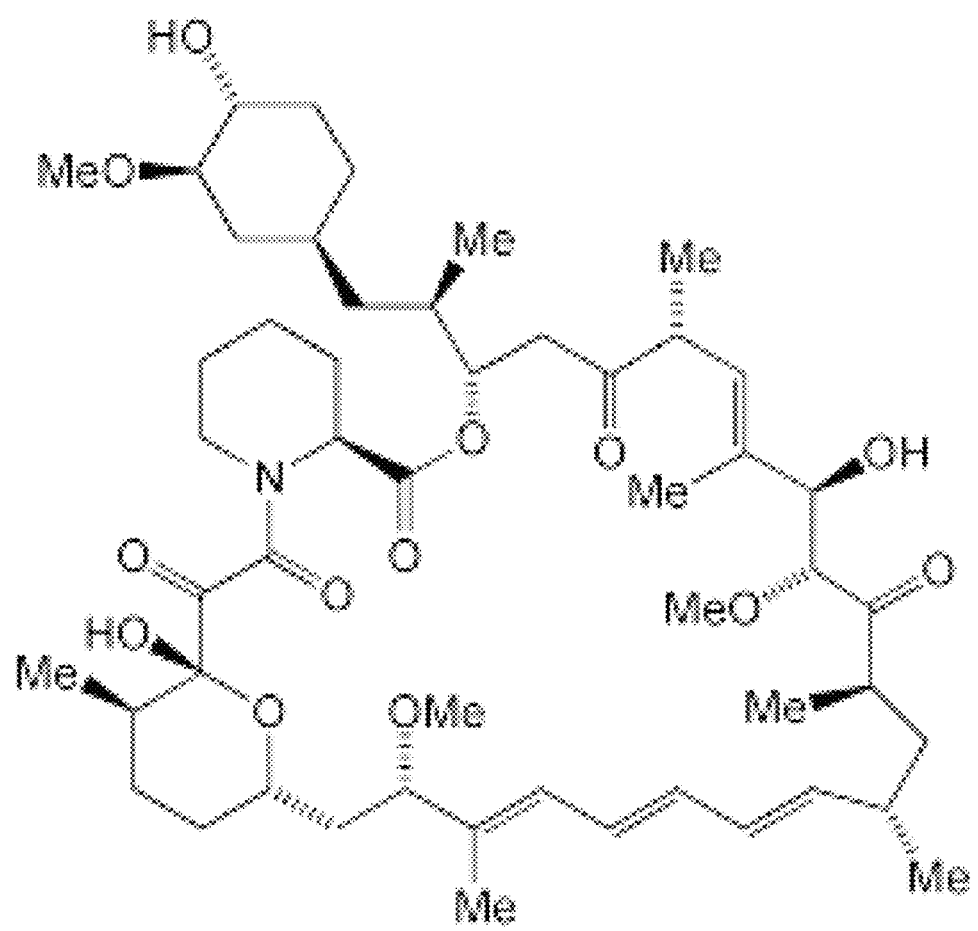
Fig. 3 – Rapamycin

TOMATIDINE

METHOD AND SYSTEM FOR REDUCING THE LIKELIHOOD OF OSTEOPOROSIS

RELATED APPLICATIONS

This application is a continuation-in-part application of U.S. patent application Ser. No. 17/011,175, filed on Sep. 3, 2020, which is a continuation-in-part application of U.S. patent application Ser. No. 16/722,117, filed Dec. 20, 2019, which is a continuation-in-part of U.S. patent application Ser. No. 16/229,252, filed Dec. 21, 2018 (now U.S. Pat. No. 10,512,661, issued Dec. 24, 2019), which is a continuation-in-part of U.S. patent application Ser. No. 15/392,173, filed Dec. 28, 2016 (now U.S. Pat. No. 10,245,288, issued Apr. 2, 2019), which is a non-provisional of U.S. Provisional Patent Application Ser. No. 62/275,341, filed on Jan. 6, 2016.

This application is a continuation-in-part of U.S. patent application Ser. No. 16/917,096, filed Jun. 30, 2020, which is a continuation-in-part of U.S. patent application Ser. No. 16/782,364, filed Feb. 5, 2020, which is a continuation-in-part of U.S. patent application Ser. No. 16/423,375, filed May 28, 2019 (now U.S. Pat. No. 10,555,976, issued Feb. 11, 2020), which is a continuation of U.S. patent application Ser. No. 16/160,336, filed Oct. 15, 2018 (now U.S. Pat. No. 10,314,866, issued Jun. 11, 2019), which is a continuation of U.S. patent application Ser. No. 15/403,823, filed Jan. 11, 2017 (now U.S. Pat. No. 10,111,913, issued Oct. 30, 2018), which is a non-provisional of U.S. Provisional Patent Application Ser. No. 62/296,186, filed on Feb. 17, 2016.

This application also is a continuation-in-part application of U.S. patent application Ser. No. 15/270,034, filed Sep. 20, 2016 (now U.S. Pat. No. 9,750,802, issued Sep. 5, 2017), which is a continuation-in-part application of U.S. patent application Ser. No. 14/954,074, filed on Nov. 30, 2015 (now issued U.S. Pat. No. 9,457,077, issuing on Oct. 4, 2016)

This application is a continuation-in-part of U.S. patent application Ser. No. 16/426,346, filed May 30, 2019 (now U.S. Pat. No. 10,716,815, issued Jul. 20, 2020), which is a continuation of U.S. patent application Ser. No. 15/639,767, filed Jun. 30, 2017 (now issued U.S. Pat. No. 10,314,865, issuing Jun. 11, 2019), which is a continuation-in-part of U.S. patent application Ser. No. 15/437,976, filed Feb. 21, 2017 (now U.S. Pat. No. 9,730,967, issued Aug. 15, 2017), which is a continuation-in-part application of U.S. patent application Ser. No. 15/228,454, filed Aug. 4, 2016 (now U.S. Pat. No. 9,585,920, issued Mar. 7, 2017), which is a continuation-in-part application of U.S. patent application Ser. No. 14/954,074, filed on Nov. 30, 2015 (now issued U.S. Pat. No. 9,457,077, issued Oct. 4, 2016).

This application is a continuation-in-part of U.S. patent application Ser. No. 16/776,861, filed Jan. 30, 2020, which is a continuation of U.S. patent application Ser. No. 16/142,171, filed Sep. 26, 2018 (now U.S. Pat. No. 10,548,761, issued Feb. 4, 2020), which is a continuation-in-part of U.S. patent application Ser. No. 15/395,419, filed Dec. 30, 2016 (now U.S. Pat. No. 10,086,018, issued Oct. 2, 2018), which is a non-provisional of U.S. Provisional Patent Application Ser. No. 62/274,550, filed on Jan. 4, 2016.

This application is a continuation-in-part of U.S. patent application Ser. No. 16/904,056, filed Jun. 17, 2020, which is a continuation-in-part of U.S. patent application Ser. No. 15/983,250 filed on May 18, 2018 (now U.S. Pat. No. 10,687,975, issued Jun. 23, 2020), which is a continuation-in-part of U.S. patent application Ser. No. 15/384,716 filed on Dec. 20, 2016 (now issued U.S. Pat. No. 9,987,224, issued Jun. 5, 2018), which claims priority of U.S. Provisional Patent Application Ser. No. 62/387,405, filed on Dec. 24, 2015.

This application also is a continuation-in-part application of U.S. patent application Ser. No. 15/270,034, filed Sep. 20, 2016 (now U.S. Pat. No. 9,750,802, issued Sep. 5, 2017), which is a continuation-in-part application of U.S. patent application Ser. No. 14/954,074, filed on Nov. 30, 2015 (now issued U.S. Pat. No. 9,457,077, issuing on Oct. 4, 2016).

The entire disclosure of the prior applications are considered to be part of the disclosure of the accompanying application and are hereby incorporated by reference.

FIELD OF THE INVENTION

The present invention is directed to the treating, preventing and reducing the likelihood of osteoporosis, with particular embodiments directed to a method employing tomatidine, xylitol, and rapamycin, as well as modifying an individual's microbiome to reduce the likelihood of osteoporosis.

BACKGROUND OF THE INVENTION

Osteoporosis is a metabolic disease that can cause pain and fragility fractures. It is a degenerative joint disease associated with chronic pain and disability involving articular cartilage breakdown, synovial inflammation, and bone hypertrophy. It is characterized by bone mass loss, microarchitectural destruction, decreasing bone mass density, increased possibility of fragility fracture, disruption of bone micro-architecture, and changes to the amount and variety of non-collagenous proteins in the bone. The incidence of senile osteoporosis increases every year, with the incidence of osteoporotic fractures of women in their 50s now at 50%. There are over a million osteoporotic fractures each year in the USA and osteoporosis has become a serious worldwide health problem.

The loss of bone mass and microarchitecture deterioration of bone tissue is attributed to various factors, including menopause, aging, and adverse effects of relevant medications. In recent decades, knowledge regarding the etiological mechanisms underpinning osteoporosis emphasizes that bone cellular homeostasis, including the maintenance of cell functions, differentiation, and the response to stress, is tightly regulated by autophagy, which is a cell survival mechanism for eliminating and recycling damaged proteins and organelles. With the important roles in the maintenance of cellular homeostasis and organ function, autophagy has emerged as a potential target for the prevention and treatment of osteoporosis. Apart from supplementation with calcium and vitamin D, the treatment for osteoporosis includes a variety of drugs with different mechanisms of actions; such drugs include bisphosphonates, selective estrogen receptor modulators, teriparatide, and denosumab. Adverse events may occur during treatment, however, including mandibular osteonecrosis, nephrotoxicity, and increased tumor risk. Therefore, novel therapeutic targets to reverse osteoporosis-related bone loss and to otherwise treat and prevent osteoporosis are urgently required.

As a progressive disease without any effective curative treatment, there is a long felt but unsolved need to find a treatment for, to prevent and to reduce the likelihood of osteoporosis so as to improve the quality of life for the many existing and future individuals who would otherwise suffer from this tragic disease.

SUMMARY OF THE INVENTION

The gut microbiota reportedly plays a key role in bone development. Aspects of the present invention are directed to the modification of person's microbiome, and particularly one's gut microbiome, to reduce the risk of osteoporosis. The gut microbiome impacts metabolic homeostasis mainly by secretion of metabolites and modulation of the host immune systems. Short chain fatty acids (SCFAs) secreted by the gut microbiome induces an increase in the transcription of calcium binding proteins in human and murine Caco-2 cells. Butyric acid regulates intestinal regulatory T cell proliferation and enhances osteoclast differentiation. In addition, the gut microbiome also maintains bone homeostasis by regulating calcium absorption-related proteins and modulating tight junction proteins.

One aspect of the present invention relates to a method for treating or preventing a bone disease or increasing bone strength in a mammalian subject comprising administering a pharmaceutical formulation that includes tomatidine, rapamycin and/or xylitol, alone or together with a probiotic composition administered to the gastrointestinal system of the individual. Preferably the probiotic bacteria include one or more of the following: *Lactobacillus reuteri, Lactobacillus acidophilus, Lactobacillus rhamnosus, Akkermansia muciniphila, Bifidobacteriaceae, F. prausnitzii, Roseburia, Veillonella*, and *Coprococcus*. Another aspect of the present invention is to reduce the numbers of certain bacteria in an individual to avoid osteoporosis, with such bacteria selected from the group consisting of *Actinomyces, Eggerthella, Clostridium* Cluster XIVa.

The gut microbiome is known to modulate immune cell activities. Alterations in the microbiome have previously been associated with inflammatory conditions. Osteoporosis occurrence is accelerated in patients with immune-mediated inflammatory conditions, where excessive production of pro-inflammatory cytokines leads to increased osteoclastic bone resorption. Thus, modifying an individual's gut microbiome to address inflammatory conditions is one route to reducing the likelihood of osteoporosis. In certain embodiments, bacteria able to generate butyrate are employed to reduce the likelihood of osteoporosis, as butyrate, as well as other short chain fatty acids, is known to stimulate bone formation. For example, in certain embodiments, the levels of *F. prausnitzii, Veillonella*, and/or *Coprococcus* are increased in an individual to treat, prevent or reduce the likelihood of osteoporosis.

One aspect of the present invention is directed to the inclusion of xylitol in various formulations and the administration thereof to individuals so as to prevent the likelihood of osteoporosis, as well as to prevent and treat the disease. Xylitol is a pentitol used as a sweetener and as a platform chemical for the production of industrially important chemicals. Xylitol has good gastrointestinal tolerance and therefore is considered safe and effective when consumed by humans. As further described below, various formulations include xylitol together with tomatidine and/or rapamycin to treat, prevent and reduce the likelihood of osteoporosis.

As described in more detail herein, one aspect of the present invention involves the use of a natural small molecule derived from tomato plants, tomatidine, to prevent and/or treat osteoporosis. Tomatidine is believed to cause cell growth, especially in skeletal muscle tissue. Tomatidine is the aglycone derivative of tomatine, an abundant glycoalkaloid in tomato plants that mediates plant defense against fungi, bacteria, viruses and predatory insects. When consumed by animals, alpha-tomatine is hydrolyzed by stomach acid and intestinal bacteria to tomatidine, which is absorbed by the gut. Tomatidine has a variety of biological activities and as described herein, is an effective agent in formulations designed to combat osteoporosis and related muscle wasting diseases.

Tomatidine is an inhibitor of muscle atrophy and thus has a use as a therapeutic agent for skeletal muscle atrophy. Tomatidine is believed to have an anti-atrophic (anabolic) effect in skeletal muscle and possesses anti-hyperlipidemic and anti-atherosclerotic effects without evidence of toxicity. Tomatidine is significantly more potent than ursolic acid in building muscle tissue and has a different mechanism of action. Tomatidine is associated with anti-apoptotic, anti-inflammatory, anti-bacterial, and anti-cancer properties. Tomatidine suppresses inflammation in LPS-stimulated murine macrophages by inhibiting the NF-κB and JNK signaling pathways.

The tomato belongs to the Solanaceae family that includes more than 3,000 species. Tomato fruit consumption has been associated with a reduced risk of inflammatory processes, cancer, and chronic noncommunicable diseases (CNCD) including cardiovascular diseases (CVD) such as coronary heart disease, hypertension, diabetes, and obesity. Tomatidine is found in certain plants at certain developmental stages, such as in green (but not ripened red) tomatoes. One aspect of the present invention is directed to the provision to individuals in need thereof with effective amounts of tomatidine to address osteoporosis.

In various embodiments of the present invention, tomatidine, alone or in combination with other agents, e.g. xylitol and/or rapamycin, is employed to reduce the likelihood of an individual experiencing osteoporosis and to otherwise treat and to also prevent the disease.

Rapamycin was first discovered in Easter Island soil bacteria in the 1980s. It is known that rapamycin extends the life span of mice. The protein that rapamycin targets is a kinase called mTOR. This kinase plays a role in a variety of pathways. Rapamycin is an inhibitor of mTOR complex (mammalian target of rapamycin) which is a serine threonine kinase and a master regulator of protein synthesis, cell growth, and cell metabolism. Excessive mTORC1 activity has been implicated in multiple disease conditions, as well as various cancers, inflammatory bowel disease, inflammatory skin diseases and neurodegenerative diseases. In various embodiments of the present invention, rapamycin is employed, especially in combination with other agents, e.g. tomatidine and xylitol, to treat, prevent and to reduce the likelihood of an individual suffering from osteoporosis.

Sirolimus (rapamycin) has to date two approved indications—renal transplantation and lymphangioleiomyomatosis and has also been shown to be potentially effective in treating Tuberous Sclerosis Complex (TSC)-associated seizures, skin disease, brain lesions, pulmonary lesions, and renal lesions. In various embodiments as described herein, administration of therapeutically effective amounts of rapamycin, directly by either aerosol administration, injection, oral administration, rectal administration, or via an individual's microbiome, forms one aspect of various embodiments of the present invention. Such employment of an anti-aging medicine like rapamycin is believed to be one of the most effective ways to combat various age-associated diseases of aging people, including osteoporosis.

In certain embodiments, DNA encoding pre-cursors for the biosynthesis of tomatidine, xylitol and/or rapamycin and its analogs is inserted into the genome of one or more bacterial species by employing CRISPR-Cas or CPf1 systems, such that an individual can orally take a pill containing such modified bacteria (preferably bacteria of the same species as presently reside in the individual's gut microbiome) and in such a manner, effectively administer tomatidine, xylitol and/or rapamycin to the individual in a manner that does not require injections or the taking of traditional pharmaceutical formulations. In such a manner, the production by such bacteria inside the individual provides a more natural way for to address the ravages of osteoporosis. Administering one or more of tomatidine, xylitol and/or rapamycin, especially in concert with the modification of an individual's gut microbiome as described herein, is able to maintain and/or restore the health of an individual, especially those subject to osteoporosis.

In certain embodiments, and while not bound by theory, it is believed that tomatidine increases the ability of an individual to not only maintain muscle mass, but to treat osteoporosis, while rapamycin, as an inhibitor of mTOR, addresses still further aspects of the disease, as does xylitol. The combination of these three ingredients in a formulation is one of a variety of preferred embodiments as disclosed herein. It is believed that these three agents may play parallel but separate roles in muscle atrophy, and thus, the use of these agents to address osteoporosis is one particular aspect of the present invention.

By administering tomatidine to an individual to maintain desired muscle mass, while also co-administering rapamycin to such individual to inhibit the growth of certain cells, especially cancer cells, one is able to achieve the seemingly converse objectives of maintaining muscle mass so as to preserve the health of an individual, while simultaneously defeating the undesired growth of cancer cells by the administration of effective amount of rapamycin to inhibit such undesired growth. Xylitol assists in halting the progression of osteoporosis, with its mechanism of action not fully understood.

The administration of such compounds/agents via an individual's microbiome is one potential way to avoid the disadvantages of other modes of administration. The administration of the described formulations of the present invention have the positive effect of extending the lifespan of an individual, and especially effective in delaying the onset of age-related diseases and conditions, such as cancer and osteoporosis, thus extending the healthspan of the individual from what it otherwise would have been if such administration was not performed. The particular effective amount of such agents/compounds, such as rapamycin, tomatidine and xylitol (including analogs or derivatives thereof) depend upon the stage of the disease, the length of duration of treatment desired and the particular characteristics of the individual's health and microbiome characteristics. One of skill in the art will understand, given the guidance provided herein, the particular aspects of administration of such formulations. In certain embodiments where the agent/compound comprises rapamycin or an analog thereof, administration of rapamycin may be performed to affect about 0.001 mg to 30 mg total per day as an effective dose, preferably at least about 0.1 mg per day, with a preferred blood level of rapamycin in the subject being about 0.5 ng per mL whole blood after administration of the composition after a 24 hour period. In embodiments where genes that encode one or more precursors for the biosynthesis of rapamycin, tomatidine and xylitol, by administering antibiotics that target the particular microbes that produce such agents/compounds/precursors, one can address overproduction by such microbes by killing the microbes producing such agents. One of ordinary skill in the art will appreciate from written materials predating this application the appropriate doses and modes of administration of any one of these three agents.

In particular embodiments, the present invention is specifically directed to a method of treating osteoporosis in a subject in need of such treatment by administering a therapeutically effective amount of a composition comprising tomatidine, either alone or in conjunction with xylitol and/or rapamycin. Other embodiments further include administering to an individual suffering from osteoporosis a therapeutically effective amount of one of xylitol, tomatidine and/or rapamycin separately, rather in a combined formulation, with the modes of administration of each of these potentially being different, e.g. one orally, one inhaled, etc.

It will be appreciated that still other aspects of the present invention involve the treatment of obesity (as well as various forms of cancer) by providing certain amounts of tomatidine via a person's microbiome to facilitate muscle mass increases, while at the same time, decreasing the amount of fat weight of the individual being administered the tomatidine.

Other aspects of the present invention relate to the reduction of the likelihood of, treatment and/or prevention of osteoporosis by interrupting a microbial pathway, and by addressing muscle atrophy associated with osteoporosis. Osteoporosis is usually managed with a class of popular drugs—bisphosphonates—that reduce bone resorption. Two of the most common orthopedic disorders are osteoporosis and osteoarthritis. In certain embodiments of the present invention, bisphosphonates are included in formulations that otherwise include tomatidine, as well as xylitol and/or rapamycin.

Various embodiments of the present invention use microbiota modifications to improve the efficacy of existing treatments, and in particular, the provision of tomatidine, alone or in conjunction with modifications to a patient's microbiome, e.g. by increasing the presence of microbes that produce SOFA, and especially butyrate, is one aspect of the present invention. Other embodiments further employ the modification of an individual's microbiome, alone or in combination with the administration of formulations that include one of tomatidine, rapamycin and/or xylitol, to treat and prevent the progression of osteoporosis. One aspect of the present invention involves the maintenance of the level of *Prevotella* in an individual as such bacterium is closely related to the occurrence of inflammatory bone loss. *Prevotella* functions through microbe associated molecular patterns (MAMPs) to activate various toll-like receptors (TLRs) and through principal immune cells to release inflammatory mediators and promote chronic inflammation. Thus, in various embodiments, the reduction in *Prevotella* can reduce the likelihood of osteoporosis. Antibiotics or the selective reduction of *Prevotella* using CRISPR-systems can be employed to achieve this objective.

Short-chain fatty acid production by commensal bacteria is important in regulating the immune system in the gut. Butyrate plays a direct role in inducing the differentiation of regulatory T cells and suppressing immune responses associated with inflammation. Butyrate is normally produced by microbial fermentation of dietary fiber and plays a central role in maintaining colonic epithelial cell homeostasis and barrier function. Various embodiments described herein promote the production of butyrate via increased numbers of beneficial bacteria (e.g. *Coprococcus, Roseburia, Bifidobacterium*, and *Faecalibacterium prausnitzii*) and/or the use of modified microbes (e.g. via the employment of CRISPR-systems) administered to an individual, alone or in concert with the various other agents as described herein to effectively treat or prevent or to reduce the likelihood of osteoporosis.

Preferably, the bacteria employed in certain embodiments of the present invention are administered orally to a patient. In certain embodiments, CRISPR engineered bacteria are used that are non-pathogenic and may be introduced into the gut in order to reduce gut inflammation and/or enhance gut barrier function. For example, in some embodiments, the bacteria are under the control of a RNS-responsive regulatory region and a corresponding RNS-sensing transcription factor such that a desired product, e.g. butyrate, is produced, which induces the differentiation of regulatory T cells in the gut and/or promotes the barrier function of colonic epithelial cells.

Still other embodiments are directed to the modification of an individual's microbiome to influence various aspects of their metabolism in a manner that not only retains and maintains the ability to nurture muscle tissue, but to also reduce obesity by affecting the amount of fat that the body stores, and further, to address the progression of osteoporosis. While not bound by theory, it is believed that the gut bacteria of an individual is a substantial source of acetate production. The production of acetate by gut microbes is believed to send signals to the brain of the individual to initiate the production of insulin, conveyed via the vagus nerve. Fine tuning of the amount and type of gut microbes (e.g. via the use of antibiotics or CRISPR systems to initially reduce the kind and numbers of undesired bacteria, followed by purposeful inoculation of an individual's gut microbiome with desired and/or modified microbes, e.g. via CRISPR-Cas insertion of particular factors, proteins, etc., such as precursors for tomatidine, xylitol or rapamycin), the administration of tomatidine and/or xylitol and/or rapamycin, etc. is an effective way to address not only muscle wasting and osteoporosis issues, but also obesity issues of individuals.

One embodiment of the present invention is directed to a bioadhesive strip adapted to bind to a mucosal membrane for at least 1 hour while inside a person's mouth, where the strip includes tomatidine and xylitol in an amount sufficient to reduce the likelihood of osteoporosis. E.g. at least 10 micro-mole of tomatidine and at least 200 mg of xylitol or at least 0.2% xylitol by weight. In preferred embodiments, the strip includes at least one polymer selected from the group consisting of pullulan, hydroxypropylmethyl cellulose, hydroxyethyl cellulose, sodium alginate, polyethylene glycol, tragacanth gum, guar gum, acacia gum, arabic gum, carboxyvinyl polymer, amylose, high amylose starch, hydroxypropylated high amylose starch, dextrin, chitin, chitosan, levan, elsinan, collagen, zein, gluten, soy protein isolate, whey protein isolate, casein and mixtures thereof.

Certain embodiments of the present invention are directed to a method for reducing the likelihood of osteoporosis in an individual human being by substantially reducing a human being's resident population of gut microbes prior to administering a therapeutically effective amount of a bacterial formulation comprising *Coprococcus*. Provision of fructan fiber inulin is preferably done in an amount sufficient to reduce the pH in the colon of the human being to achieve acidifying of the colon, which also supports the maintenance of the *Coprococcus* bacteria. In preferred embodiments, the beneficial formulation is encapsulated. Such encapsulation is done to preserve the viability of various bacteria that would otherwise be adversely affected by stomach acids and/or aerobic environments. See, e.g. U.S. patent Ser. No. 10/576,113 Madhavamenon, et. al, incorporated herein by this reference. In still other embodiments, the *Coprococcus* bacteria employed are first isolated from a human being's stool and are from the human being treated. One important aspect of certain embodiments of the present invention involves the administration of tomatidine to the human being to combat osteoporosis, with formulations thereof similarly encapsulated to preserve potency and efficacy. In still other embodiments, the method for reducing the likelihood of osteoporosis involves the use of bacteria modified via a clustered regularly interspaced short palindromic repeats (CRISPR) CRISPR associated protein (Cas) system or a CRISPR from *Prevotella* and *Francisella* 1 (Cpf1) system. For example, CRISPR systems can be used to selectively reduce the numbers of certain bacteria often found associated with osteoporosis, such as *Actinomyces, Eggerthella*, and *Clostridium* Cluster XIVa. In other embodiments, there is a reduction of bacteria in the gut of the human being, wherein the bacteria reduced are selected from the group consisting of *Pediococcus, Streptococcus, Enterococcus*, and *Leuconostoc* bacteria.

In particular embodiments, the step of reducing the number of bacteria comprises administering an antibiotic. Moreover, reducing the number of bacteria in the human being's gut using a clustered regularly interspaced short palindromic repeats (CRISPR) CRISPR associated protein (Cas) system or a CRISPR from *Prevotella* and *Francisella* 1 (Cpf1) system is effective and has advantages over the use of a general antibiotic. In preferred embodiments, inclusion of a bacterium selected from the group consisting of *Chlamydia, Shigella flexneri, Mycoplasma* bacteria, *Lactobacillus casei, Roseburia, Bifidobacterium*, and *Faecalibacterium prausnitzii* is accomplished to reduce the likelihood of osteoporosis. Another aspect of the present invention is directed to increasing the levels of bacterial genera selected from the group consisting of *Bifidobacterium, Lachnospira, Roseburia, Lactobacillus* and *Shigella*.

In still further embodiments, a population of beneficial bacteria selected from the group consisting of *Coprococcus, Roseburia, Bifidobacterium*, and *Faecalibacterium prausnitzii*, is administered, as well as fiber to the individual to maintain a therapeutically effective amount of the beneficial bacteria in the gut of the individual. The individual is then administered at least 10 micro-mole of tomatidine.

In other embodiments, the gut of the individual is provided with a *Lactobacillus* species and at least 6 grams per day of fiber to maintain a therapeutically effective amount of the beneficial bacteria in the gut of the individual human being. Preferably, in still other embodiments, the levels of at least one of *Roseburia* and *Faecalibacterium prausnitzii* are increased in the individual's gut microbiome. In some embodiments the step of reducing the number of bacteria in the human being is achieved using an antibiotic or using a clustered regularly interspaced short palindromic repeats (CRISPR) CRISPR associated protein (Cas) system or a CRISPR from *Prevotella* and *Francisella* 1 (Cpf1) system to selectively kill or reduce the number of undesired bacteria. In other embodiments the levels of bacteria are increased, such bacteria selected from the group consisting of *Bifidobacterium, Prevotella, Lachnospira*, and *Shigella*, alone or together with the administration of at least one of xylitol, tomatidine and rapamycin. Certain embodiments of the invention are directed to providing in the gut of an individual a population of beneficial bacteria selected from the group consisting of *Faecalibacterium prausnitzii* and/or *Akkermansia muciniphila*; administering at least 6 grams per day of fiber to the individual to maintain a therapeutically effective amount of the beneficial bacteria in the gut of the individual human being; and administering tomatidine (in an effective amount) to the individual human being. In still other embodiments, the present invention includes administering to the individual human being a bacteria selected from the group consisting of *Streptococcus, Actinomyces, Veillonella, Fusobacterium, Porphyromonas, Prevotella, Treponema, Neisseria Haemophilus, Lactobacillus, Capnocytophaga, Eikenella, Leptotrichia, Peptostreptococcus, Propionibacterium, Chlamydia, Shigella flexneri, Mycoplasma bacteria, H. pylori,* and *Streptomyces hygroscopicus.* To reduce the likelihood of osteoporosis, various embodiments include administering to an individual an effective amount of a formulation comprising at least two of: at least 10 micro-mole tomatidine, at least 0.1 mg of rapamycin and at least 200 mg of xylitol. Particular embodiments employ an oral strip to deliver the agents as described herein. For example, one embodiment involves the administration of one of tomatidine, xylitol and rapamycin to individuals by using a bioadhesive strip having a first and second side, the second side having a bioadhesive that is adapted to bind to a mucosal membrane for at least 1 hour while inside a person's mouth. Such strip includes at least one polymer selected from the group consisting of pullulan, hydroxypropylmethyl cellulose, hydroxyethyl cellulose, sodium alginate, polyethylene glycol, tragacanth gum, guar gum, acacia gum, arabic gum, carboxyvinyl polymer, amylose, high amylose starch, hydroxypropylated high amylose starch, dextrin, chitin, chitosan, levan, elsinan, collagen, zein, gluten, soy protein isolate, whey protein isolate, casein and mixtures thereof; wherein said strip includes one of tomatidine or xylitol.

One will appreciate that this Summary of the Invention is not intended to be all encompassing and that the scope of the invention nor its various embodiments, let alone the most important ones, are necessarily encompassed by the above description. One of skill in the art will appreciate that the entire disclosure, as well as the incorporated references, figures, etc. will provide a basis for the scope of the present invention as it may be claimed now and in future applications. While embodiments of the invention have been illustrated and described, it is not intended that these embodiments illustrate and describe all possible forms of the invention. Rather, the words used in this specification are words of description rather than limitation, and it is understood that various changes may be made without departing from the spirit and scope of the invention.

BRIEF DESCRIPTION OF THE FIGURES

FIG. 1 is an illustration of the effects of osteoporosis on human bones.
FIG. 2 is the chemical formula for xylitol.
FIG. 3 is the chemical formula for rapamycin.

DETAILED DESCRIPTION OF EMBODIMENTS OF THE PRESENT INVENTION

Figure 4:
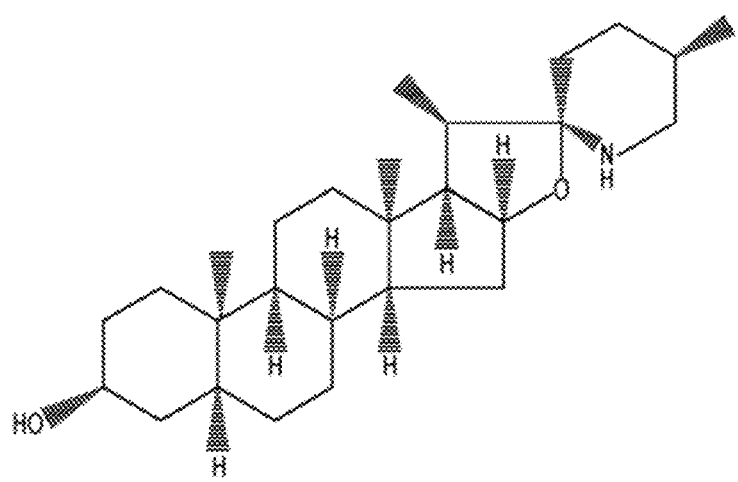
FIG. 4 is the chemical formula for tomatidine.

Osteoporosis is a disease associated with the aged. During aging a wide spectrum of alterations in mitochondrial structure and function can occur. Mutational damage accumulates over lifetime, in particular affecting respiratory chain complexes, which results in the overproduction of ROS and leads to mitochondrial dysfunction. Aging reveals that mitochondria become enlarged, have irregular shapes and decrease in number. One aspect of the present invention is to both prevent and treat osteoporosis. Certain embodiments are directed to treating and extending an individual's healthspan to combat the ravages of certain age related diseases, such as osteoporosis. In certain embodiments, the provision of effective amounts of tomatidine is used to treat or prevent osteoporosis.

Postmenopausal osteoporosis is initiated by estrogen withdrawal and is characterized mainly by over-activated osteoclastic bone resorption. While not bound by theory, it is believed that tomatidine inhibits osteoclast formation in a dose-dependent manner and decreases the expression of osteoclast marker genes. Tomatidine appears to attenuate osteoclast formation and function by modulating multiple pathways. Also, while not bound by theory, it is believed that tomatidine plays a role in mitigating osteoporosis by inhibiting osteoclastogenesis and reducing estrogen deficiency-induced bone mass loss. Tomatidine also plays a biological role of mitigating apoptosis by inhibiting the expression of p53.

There is increasing evidence that mitophagy is significantly impaired in several human pathologies including aging and age-related diseases such as neurodegenerative disorders, cardiovascular pathologies, cancer and bone related diseases. Therapeutic interventions aiming at the induction of mitophagy is believed to have the potency to ameliorate these dysfunctions. As described herein, one therapeutic intervention is the administration to an individual of a formulation that includes at least two of tomatidine, xylitol and rapamycin to treat, prevent and to reduce the likelihood of osteoporosis.

Mitochondria originated from endosymbiotic proteobacteria and conferred substantial advantages for eukaryotic cells during evolution. Mitochondria play a critical role in ATP synthesis via oxidative phosphorylation (OXPHOS), β-oxidation regulating fatty acid metabolism, the synthesis of intermediate metabolites through the TCA cycle, as well as calcium homeostasis. On the other hand, mitochondria are the central organelle controlling apoptotic cell death and the permeabilization of the mitochondrial outer membrane releases pro-apoptotic proteins such as cytochrome c, SMAC/DIABLO, ENDOG, OMI/HTR and AIF, which leads to cellular demise. Mitochondria are the major source of reactive oxygen species (ROS) which can oxidize proteins, lipids, and nucleic acids, inside (and outside) the mitochondria, leading to mitochondrial malfunction and cellular damage. Mitochondria serve as an origin of damage associated molecular patterns (DAMP) and in particular mitochondrial DNA (mtDNA), which, once released from mitochondria into the cytosol, can trigger inflammatory responses.

Autophagy is a conserved intracellular degradation mechanism that removes dangerous, unnecessary or dysfunctional cytoplasmic constituents and invading microbes. Autophagic activity declines during aging, and autophagy is required for lifespan extension by caloric restriction or caloric restriction mimetics (CRM) such as resveratrol, spermidine, and several chalcones. Mitophagy plays a key role in delaying aging and age-related disorders such as neurodegenerative disorders, cardiovascular pathologies, and cancer. One aspect of various embodiments of the present invention is directed to therapeutic interventions that harness mitophagy to treat age-related disorders.

The KEGG pathways involved in osteoporosis are associated with tomatidine-targeted genes, such pathways including chronic myeloid leukemia, B cell receptor signaling, cancer, bladder cancer, and progesterone-mediated oocyte maturation. These pathways are also involved in the p53 signaling pathway and the MAPK signaling pathway. It is believed that the downregulating of p53 expression may be protective for osteoporosis. Tomatidine administered to an individual who suffers from osteoporosis improves their lives by treating osteoporosis, with one of tomatidine's mechanisms of action achieved by modulating p53.

Rapamycin, an allosteric inhibitor of mechanistic target of rapamycin (mTOR), prevents age-related conditions in humans. mTOR is a critical nutrient sensor and has multiple downstream effects, including protein synthesis, and autophagy. Eliminating damaged mitochondria via mitophagy is believed to be a mechanism responsible for the beneficial effects of rapamycin. Rapamycin enhances mitophagy.

Mitochondria are important for cellular life and death and mitophagy is the mechanism to preserve for mitochondrial quality and quantity control. Dysfunction of mitochondria is a characteristic of aging and age-related disease and mitophagy counterbalances age-related pathological conditions. Thus, one aspect of the present invention is directed to stimulation of mitochondrial turnover by enhancing mitophagy to treat and prevent (or delay) age-related diseases and to extend healthspans and lifespans.

The positive effects of tomatidine on muscle mass are accompanied by increased strength and exercise capacity, as well as increased specific force, which shows that tomatidine may have a greater effect on strength than muscle mass. Aspects of the present invention are directed to both the avoidance of muscle atrophy while also reducing the likelihood of osteoporosis.

As used herein, the terms "effective amount" and "amount effective" refer to an amount that is sufficient to achieve the desired result or to influence an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products, such as xylitol, rapamycin and tomatidine. In further various aspects, a preparation can be administered in a "prophylactically effective amount"; that is, an amount effective for prevention of a disease or condition. In various embodiments, an effective amount of rapamycin may be 50 to 250 micrograms; or between 0.1% to 20% of rapamycin based on total weight of the formulation; or at least 0.1 mg of rapamycin; or a dose of rapamycin in the range of 1 mg/day to 5 mg/day, and in other embodiments, in the range from about 0.01 .mu.g/day to about 50 .mu.g/day. In certain embodiments, the effective amount of tomatidine is at least 10 micro-mole of tomatidine; and at least 200 mg of xylitol or at least 0.2% xylitol by weight.

Tomatidine is present in high amounts in the unripe green tomato and in much lower amounts in the ripe red tomato. This is consistent with a role for tomatidine in protecting the unripe tomato against consumption, with the reduction in tomatidine levels in the ripe fruit then enabling consumption of the fruit and dispersal of the seeds by the consumer. Moderate amounts of tomatidine can activate adaptive cellular stress responses in muscle cells and thus, counteract age-related dysfunction and degeneration.

While not bound by theory, it is believed that such administration of tomatidine extends the lifespan and healthspan of humans and other mammals by inducing mitochondrial hormesis via the induction of ROS production. This further entails the activation of certain cellular and antioxidant pathways, including the SKN-1/Nrf2 pathway, which results in increased mitophagy. The selective removal of damaged or dysfunctional mitochondria by mitochondrial autophagy, termed mitophagy, is believed to be a feature of a treatment to extend an individual's lifespan in a safe and effective manner. Mitophagy modulates bioenergetics and survival in various diseases by reducing redox and damage. Impaired mitophagy occurs in physiological aging, as well as in certain diseases, such as sarcopenia and also believed to be present in cachexia. In certain embodiments, the administration or delivery of certain noxious chemicals are believed to counteract aging and age-related disease by inducing adaptive hormetic stress responses in cells. In other embodiments, the inclusion of rapamycin administration is employed to improve the healthspan of humans as it is further related to mitophagy. The methods and systems as set forth herein are directed to the extension of human life span in a fashion that promotes healthy aging and counteracts disease processes related to age-related disease, including but not limited to osteoporosis.

Tomatidine administration as described in the present specification is believed to contribute to a delay in the physiological aspects of aging, and thus, is able to prevent, treat and reduce the likelihood of osteoporosis. For example, it is believed that tomatidine increases mitochondria DNA content and muscle fitness and lowers adiposity, as well as decreases skeletal muscle atrophy. While not bound by theory, it is believed that the administration of tomatidine maintains homeostasis by modulating mitochondrial biogenesis and induces mild oxidative stress, which activates the above referenced pathways to induce mitophagy. The amount of tomatidine administered is believed to be important to achieve its desired age fighting effects, with at least about 10 micro-mole, and more beneficially with between about 25 micro-mole and 50 micro-mole being preferred. Moreover, administration of tomatidine is believed to increase the production in an individual of amounts of certain amino acids, such as free amino acids of leucine, threonine, tryptophan, arginine, histidine, valine, isoleucine, and methionine. Such administration is also believed to affect ROS regulation and metabolism. As aging is known to negatively affect mitochondrial quality and biogenesis, the use of tomatidine to enhance mitophagy can be employed to reduce the amount of neurodegeneration and cellular dysfunction of cell metabolism, especially by inducing an increase in Nrf2/ARE reporter activity. Upon activation by ROS, Nrf2 translocates from the cytoplasm of a cell to the nucleus, where it binds to the ARE region to transcriptionally activate genes encoding antioxidant proteins. Thus, tomatidine administration activates the Nrf2-ARE pathway by inducing cells to increase levels of ROS, resulting in the contribution to mitophagy induction. While not bound by theory, it is also believed that administration of tomatidine as described herein acts via multiple stress response pathways, such as, in addition to the Nrf2 pathway referenced above, through the activation of the mitochondrial unfolded protein response (UPR mt). Compromised mitochondrial quality and function is related to pathological aging and disease and the accumulation of damaged mitochondria within cells triggers apoptosis, inflammation and cell senescence. Sarcopenia is observed in aging individuals, with almost 25% of those over 60 years old experiencing the same, rising to over 50% by the age of 80. Tomatidine is believed to preserve muscle function during aging and therefore extends lifespan by improving mitochondrial quality by reducing muscle atrophy. Sarcopenia is therefore common in aging and is associated with the deterioration of muscle fiber cells and with infiltration of adipocytes and inflammatory immune cells, impairing the generation of new myocytes. In various embodiments of the present invention, the employment of tomatidine is not resultant from effects on muscle stem cells or immune cells, but rather, is directed to the effect that tomatidine has in influencing the muscle cells themselves as it is believed that the mechanism of action is directed to processes occurring within skeletal muscle fiber cells.

Various aspects of the present invention are directed to the induction of mitophagy by the administration of tomatidine, especially via the microbiome cells of an individual as otherwise described herein, so as to enhance the quality of the cellular mitochondrial pool and/or mitochondrial biogenesis. Support for this theory of action can be found, for example, in studies of premature aging disease, such as Hutchinson-Gilford progeria syndrome, caused by a mutation of the nuclear architectural proteins lamin A and C. Such patients showed profound growth delay and premature aging phenotypes, including cardiac muscle and skeletal muscle pathologies. It is known that Nrf2 activity contributes to premature aging and that activation of the Nrf2 pathway ameliorates such disease. One aspect of the present invention is therefore directed to the administration of tomatidine, in particular as described herein via expression by or in conjunction with various bacteria in an individual's microbiome, so that it triggers mitophagy and induces Nrf2 activation. A signaling role for ROS in the stimulation of mitophagy in cells under mild stress supports the use of tomatidine as described herein, as moderately elevated ROS levels have been seen as inducing mitophagy, which has the effect of clearing aged or dysfunctional mitochondria. If ROS levels are too high, however, or if mitophagy is compromised, mitochondrial dysfunction becomes exacerbated, demonstrating that ROS levels have a dynamic role in health and aging disease. Employment of tomatidine to achieve a moderate elevation of ROS levels is therefore one objective of various embodiments of the present invention, but with care not to achieve excessive ROS levels, thus accomplishing the desired goal of enhancing cellular stress resistance in a manner that is disease protective. Tomatidine is therefore preferably administered in effective amounts that induce a moderate increase in ROS levels that is necessary to trigger mitophagy without demonstrating mitochondrial dysfunction.

Tomatidine is not believed to have significant anti-microbial effects, at least when used alone. When co-administered with other compounds, however, it is believed that there is a synergistic effect and therefore, tomatidine is viewed as an antibiotic potentiator when used with ampicillin, etc. Preferably, tomatidine, in certain embodiments is used at a concentration of about 200 micro grams per mL. Thus, in several embodiments, the use of tomatidine administration in an individual is employed to synergistically enhance the action of various antibiotics against certain bacteria. Such synergistic effects are believed to be also accomplished when tomatidine expression/administration in an individual is coupled of the co-administration with at least one of the following: p53 protein, rapamycin, resveratrol, metformin, spermidine, xylitol, glucosamine and methylene blue.

Short-chain fatty acid production by commensal bacteria is important in regulating the immune system in the gut. Butyrate plays a direct role in inducing the differentiation of regulatory T cells and suppressing immune responses associated with inflammation. Butyrate is normally produced by microbial fermentation of dietary fiber and plays a central role in maintaining colonic epithelial cell homeostasis and barrier function. Use of such modified bacteria, especially those modified via CRISPR-Cas systems, provides a way to generate a desired therapeutic effect in a manner that lowers the safety issues associated with systemic exposure. Importantly, the increase in butyrate and other SCFA's should be accomplished only if an individual's gut barrier function has not been compromised as high systemic concentrations of propionate and butyrate may otherwise lead to adverse effects, such as increased serum levels of SCFAs due to the enhanced "leak" of the gut barrier.

Resveratrol (3,4',5-trihydroxystilbene; $C_{14}H_{12}O_3$) is a polyphenolic phytoalexin found in grapes, berries, peanuts, and wines. Resveratrol has been viewed as an antioxidant, anti-inflammatory, anti-apoptotic, and anticancer agent. Moreover, it has been reported that resveratrol modulates mitochondrial function, redox biology, and dynamics in both in vitro and in vivo experimental models. Resveratrol also attenuates mitochondrial impairment induced by certain stressors. Resveratrol upregulates, for example, mitochondria-located antioxidant enzymes, decreasing the production of reactive species by these organelles. Resveratrol also triggers mitochondrial biogenesis, ameliorating the mitochondria-related bioenergetics status in mammalian cells. Brain cells (both neuronal and glial) are susceptible to mitochondrial dysfunction due to their high demand for adenosine triphosphate (ATP). Additionally, brain cells consume oxygen ($O_2$) at very high rates, leading to a proportionally high mitochondrial production of reactive species. One aspect of various embodiments of the present invention is the maintenance of mitochondrial function in various cell types to address degenerative diseases, which involve mitochondrial impairment and increased generation of reactive species, leading, for example, to neuroinflammation and cell death. The mechanism by which resveratrol protects mitochondrial function and dynamics is not completely understood, but it is known that resveratrol is able to induce cytotoxicity depending on its dosage. Resveratrol produced by the microbiome of an individual (or precursors thereof) can be employed to improve the dysregulation of the gut microbiota induced by a high-fat diet, as it results in increasing the ratio of *Bacteroides*-to-Firmicutes and also increases the growth of *Lactobacillus acidophilus* and *bifidobacterium* in humans. It is believed that resveratrol modifies the intracellular environment by changing the oxidizing milieu into a reducing milieu and upregulates intracellular glutathione, potentiating a signal transduction cascade that results in mitophagy, and thus paves the way to an anti-aging environment.

Mammalian/mechanistic target of rapamycin (mTOR) is an intracellular protein complex that is responsive to both growth factors and nutrient availability, and which also impacts mitochondrial function. It is comprised of the TOR kinase—known as mTOR in mammals. The TOR signaling pathway is highly conserved in eukaryotes and is functionally defined as the target of the highly-specific antifungal, rapamycin. mTOR and aging appear to have co-evolved, suggesting that cancer is inexorably linked to fundamental aspects of life. Rapamycin can be employed, via production by or used in conjunction with an individual's microbiome, to achieve the objective of delaying the effects of aging and thus, reduce diseases associated with aging, including osteoporosis. Age-associated diseases interface with TOR and its signaling systems, and thus, employment of rapamycin (alone or in concert with the various other agents described herein) provides the ability to target both aging and its associated diseases, including osteoporosis.

In certain embodiments, precursors of one of xylitol, rapamycin and tomatidine are administered via an individual's own microbiome as a way to deliver a therapeutic treatment that works on everyone despite the distinct and acknowledged differences between an individual's microbiome. The differences of each individual's microbiome works in favor of this approach as delivery of rapamycin via one's own microbiome is naturally customed tailored as focusing on modification of an individual's microbiome provides desired anti-aging agents while maintaining the distinct character of an individual's microbiome. Aging is therefore possible to treat in a personalized way by taking into account the individual's unique microbiome. The present invention provides a way to tailor preventive measures and treatments to different individuals. Mechanical loading plays a major role in the regulation of skeletal muscle mass, and the maintenance of muscle mass profoundly influences health and quality of life. Signaling by the mammalian/mechanistic target of rapamycin (mTOR) is a key component of the mechanotransduction pathway. Employment of an individual's microbiome to administer effective amounts of rapamycin to the individual is one way in which to modulate mTOR signaling, thus affecting muscle mass and associated bone density.

A variety of stimuli, such as nutrients, growth factors, and mechanical loading, can regulate protein synthesis in skeletal muscle. The regulation of translation initiation by these stimuli is mediated by mTOR, which exists in at least two characteristically distinct complexes; a) the rapamycin-sensitive mTOR complex 1 (mTORC1), and b) the rapamycin-insensitive mTOR complex 2 (mTORC2). The control of translation initiation by mTOR is one of the key steps for the regulation of protein synthesis in skeletal muscle. Rapamycin, a highly specific inhibitor of mTOR signaling, can prevent protein synthesis induced by various forms of mechanical loading such as resistance exercise. Rapamycin can prevent chronic mechanical overload-induced increases in fiber size (i.e., hypertrophy). Rapamycin-sensitive mTOR signaling plays a central role in the regulation of protein synthesis and muscle mass during periods of increased mechanical loading. mTOR is the rapamycin-sensitive element that confers mechanically induced muscle growth. Rapamycin exhibits growth inhibitory effects. mTOR, within skeletal muscle cells, is the primary rapamycin-sensitive element that confers a mechanically-induced hypertrophic response. The targeting of mTOR signaling is therefore critical in various methods directed to the prevention of muscle atrophy. mTOR is a crucial component in the mechanotransduction pathway that promotes muscle growth. mTOR signaling induces skeletal muscle growth via a rapamycin-sensitive mechanism. Mechanical loading activates mTOR signaling and muscle growth through a unique mechanism but the identity of this mechanism remains unclear.

Administration of formulations that include at least one of and more preferably two of the following: xylitol, tomatidine and rapamycin, and especially when an individual's microbiome is modified to achieve increased amounts of butyrate production (as compared to pre-treatment levels) can therefore mitigate osteoporosis and therefore treat, prevent and/or reduce the likelihood of the disease.

Skeletal muscles consume a lot of energy (i.e., ATP) during every cyclic interaction between actin and myosin, and importantly, these active muscles comprise approximately 45% of total body mass. As mitochondria are the source of ATP in humans and in view of the importance of mitophagy as described herein, the link between rapamycin and tomatidine with mitochondria and the retention of muscle mass of an individual can be discerned.

Skeletal muscles can also play a critical role in the regulation of whole-body energy metabolism. Skeletal muscle mass is inversely associated with several metabolic disorders such as obesity, diabetes, and metabolic syndromes. Thus, the maintenance of skeletal muscle mass is not only keeping human bodies physically functional, but also metabolically healthy. As skeletal muscle functions are directly associated with its mass, and thus, the maintenance of skeletal muscle mass will contribute significantly to health and quality of life. Skeletal muscle mass is reduced with aging and both sedentary and active adults will lose up to 30-40% of their muscle mass, which is directly related to and is associated with disability, loss of independence, an increased risk of morbidity and mortality. While it is known that skeletal muscle mass can be increased by mechanical loading/stimuli (e.g., mechanical overload, etc.) in many individuals, there are problems with achieving such stimuli, including the simple human propensity for the avoidance of exercise. The present invention, in various aspects, provides an alternative, as well as a co-treatment, for those individuals who cannot or who do not engage in mechanical loading/stimuli to preserve their muscle mass as they age, thus preventing muscle atrophy.

It has been observed that caloric restriction in a variety of organisms—including mice, flies, worms, and yeast—achieves an extended life span and activates cellular protection pathways. In humans, however, caloric restriction often results in a weakening of the immune system. In any event, it is a largely impracticable way to realistically achieve the goals of a long and healthy life. The present invention provides a better way. A comparison of stools from aged vs. young humans reveals that older frail folks had lower levels of short-chain fatty acids, which the microbes in our guts normally make from dietary fiber. These short-chain fatty acids, including acetate, butyrate, and propionate, are an important energy source for the colon. Frail subjects also had gut microbiomes depleted in species of bacteria that could do this chemical conversion. It has also been observed that cancerous cells often become senescent and secrete chemical messages to nearby cells, all the while ceasing division. When enough senescent cells accumulate, their combined chemical cocktail results in a variety of age-related problems, including osteoporosis.

Mitochondria are critical in understanding aging, as demonstrated by some of the first genes found to extend worm lifetimes coding for dysfunctional proteins in mitochondria. The shortening of telomeres is also associated with aging, but attempts to use telomerase to help rebuild shortened ends often results in cancer. For most of human evolutionary history, a human's life span was extremely short and therefore, few died of old age diseases, such as cancer or heart disease. Evolution optimized most human traits so we could survive long enough to produce offspring. In the late 1990s, researchers discovered that simple mutations in single genes could double, triple, and even more radically increase the life span of worms and single gene mutations were also found that could extend life span in fruit flies and mice and other organisms. Some therefore believe that because simple genetic interventions can extend lifetimes and healthspans, targeting such genes will result in addressing aging. But such a route entails undesired human genetic manipulation. The present invention avoids such a dramatic tactic and achieves the desired and long-sought anti-aging objective via manipulation of an individual's microbiome, rather than their human DNA.

The process of oxidative phosphorylation for ATP generation in mitochondria is the main source of reactive oxygen species (ROS) within the cell (about 90% of total ROS in cells). The limited repair capacity of mitochondrial DNA (mtDNA) makes them particularly vulnerable to accumulation of damages, with mutations in mtDNA resulting in increased ROS production, which causes diverse damages in the cells. The ROS vicious cycle is believed to account for an exponential increase in oxidative damage during aging. Senescent cells also increase with age and have been found at sites of age-related pathologies. Chronically active p53 both promotes cellular senescence and accelerates aging phenotypes.

One prominent response of cells to tomatidine is induction of mitophagy, which preserves cellular function during aging. Mitochondrial dysfunction and defective mitophagy are implicated in the etiology of several major age-related diseases. Certain aspects of the present invention are directed to alterations of an individual's microbiota in terms of the particular composition, diversity and functional features of the intestinal microbiota to combat chronic inflammation and various aging-associated pathologies. Such modification of an individual's microbiome, whether it be skin, oral, vaginal, but especially intestinal gut microbiota, is performed in a manner to favorably enhance antioxidant activity, improve immune homeostasis, suppress chronic inflammation, and regulate fat metabolism.

To comply with written description and enablement requirements, all references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material. Incorporated herein by this reference are the following US patent publications: 20170079947 to Richards; 20140296139 to Cohen et al.; 20160175327 to Adams et. al.; 20100081681 to Blagosklonny and 20120283269 to Blagosklonny; U.S. Patent Publication Nos. 20140030332 to Baron, et al., 20070123448 to Kaplan et al.; 20160000841 to Yamamoto, et al.; 20160095316 to Goodman et al.; 20160158294 to Von Maltzahn; 20140294915 to Kovarik; U.S. Pat. No. 8,034,601 to Boileau et al.; 20130225440 to Freidman, et al., 20150071957 to Kelly et al., 20160151428 to Bryann et al.; 20160199424 to Berry et al.; 20160069921 to Holmes, et al.; 20160000754 to Stamets; U.S. Pat. No. 9,044,420 to Dubensky, Jr, et al.; 20160120915 to Blaser et. al.; 2014/0349405 to Sontheimer; 2014/0377278 to Elinav; 2014/0045744 to Gordon; 2013/0259834 to Klaenhammer; 2013/0157876 to Lynch; 2012/0276143 to O'Mahony; 2015/0064138 to Lu; 2009/0205083 to Gupta et al.; 201/50132263 to Liu; and 2014/0068797 to Doudna; 2014/0255351 to Berstad et al.; 2015/0086581 to Li; PCT/US2014/036849 and WO 2013026000 to Bryann; U.S. Pat. Publication No. 2015/0190435 to Henn; 2012/0142548 to Corsi et al.; U.S. Pat. Nos. 6,287,610, 6,569,474, U.S.2002/0009520, U.S.2003/0206995, U.S.2007/0054008; and U.S. Pat. No. 8,349,313 to Smith; U.S. Pat. No. 9,011,834 to McKenzie; 20150004130 to Faber et. al, 20160206666 to Falb; 20160206668 to Kort et. al; and WO2015069682A2 to Asesvelt, et. al.; 20160199424 to Berry et al.; 20130326645 to Cost et al.; 2012/0276149 to Littman; and U.S. Pat. No. 9,314,489 to Kelly et. al.; 20160243132 to Adams, et. al.; U.S. Pat. No. 9,549,842 to Kovarik; 20200032224 to SCHAEFER et. al.; 20170014341 To Armer, et. al. and U.S. Pat. No. 10,683,323 to Prakash, et. al.

Proper functioning of mitochondria, as the central organelle for metabolism and other cell signaling pathways, is required to maintain rapid growth and proliferation of cancer cells since tumor cells devoid of mitochondria grow very slowly. Increased amounts of lactate not only blocks acetyl-CoA metabolism in mitochondria, but also reduces mitochondrial biogenesis as well as oxygen consumption. Tumor suppressor, P53, plays an important role in promoting cell death as it is activated via a ROS-dependent pathway and leads to apoptosis in cancer. Inhibited cell growth and increased apoptosis in cancer by P53 activation are also regulated by miRNA or SIRT2 dependent pathways. Lactate-producing cancer cells are characterized by increased aerobic glycolysis and excessive lactate formation, a phenomenon described by Otto Warburg 93 years ago, which still remains unexplained. In 1923, Otto Warburg observed that cancer cells were characterized by accelerated glycolysis and excessive lactate formation even under fully oxygenated conditions. His discovery was subsequently named the 'Warburg Effect'. While the Warburg Effect is a hallmark of cancer, the study of cancer cell metabolism was diverted when investigators began to employ genomic techniques to better understand cancer biology. The cure for cancer through gene-based research, however, has yet to come to fruition, and the role of the Warburg Effect in cancer growth and carcinogenesis is still a mystery. One aspect of the present invention relates to the production of various agents by an individual's microbiome, including the use of lactobacterium that produce lactate. There has been a recent renewal of interest in lactate as a player in cancer as lactate is an obligatory product of glycolysis, an important metabolic fuel energy source, and an important signaling molecule. In lactagenic cancers, there is observed a decrease in mitochondrial function. Lactate production constantly occurs in skeletal muscles as lactate is the obligatory product of glycolysis. The rate of lactate production is greatly enhanced in working skeletal muscles and thus, it has been observed that during high-intensity exercise, working muscles display some of the same metabolic characteristics as do cancer cells. Certain aspects of the present invention are therefore directed to the employment of lactobacterium via introduction into an individual's microbiome, such that the levels of lactate can be achieved to address lactate metabolism. Damaged mitochondria are responsible for increased production of reactive oxygen species, metabolic inflexibility, and inflammation.

A number of compounds have been found to stimulate autophagy, including rapamycin, resveratrol, metformin, spermidine, and glucosamine. mTOR, the mammalian target of rapamycin, is considered to be a major checkpoint in a pathway linking the cellular nutritional state with the level of ongoing autophagy. Mitochondria can be selectively targeted for degradation via macroautophagy (mitophagy). Induction of autophagy is an important homoeostatic mechanism that is disrupted in dystrophic muscles. Autophagy promotes osteogenic differentiation of human bone marrow mesenchymal stem cells. Rapamycin is a well-characterized autophagy stimulator. The mTOR pathway is involved in promoting anabolic processes, ribosome biogenesis, protein synthesis and many cellular pathways, inhibiting cell stress responsive pathways, and protein degradation by autophagy. Inhibiting mTOR with agents such as rapamycin retards protein synthesis and enhances cell stress responsive pathways, such as autophagy.

Treatment with rapamycin and rapalogs (rapamycin analogues) and the role of mTOR signaling via the mTORC1 complex on osteoclast, osteoblast, and osteocyte differentiation and function is generally considered to be a largely bone-sparing drug which may improve compromised bone quality. One aspect of the present invention relates to an individual's treatment with rapamycin to restore osteoblast differentiation and bone volume and to reduce the severity of senile osteoporosis. It is believed that rapamycin's stimulation of autophagy provides a clinical approach in the treatment of osteoporosis. Rapamycin-induced autophagy improves bone fracture healing and has beneficial effects on the trabecular compartment of long bones. Certain embodiments employ a dose of rapamycin in the range of 1 mg/day to 5 mg/day, and in other embodiments, in the range from about 0.01 .mu.g/day to about 50 .mu.g/day.

Autophagy is a cellular process that degrades damaged proteins and mitochondria. The failure of this process in the elderly to effectively rid the body of such damaged proteins and organelles leads to the age-associated malfunctions of many biological processes. Mitochondria is an intracellular signaling organelle that communicates with the rest of the body to regulate metabolism and cell fate and thus, manipulation of mitochondria is believed to be involved in addressing a majority of age-related diseases, including osteoporosis. Mitochondria have their own small collection of genes, which were once thought to play only minor roles within cells but now appear to have important functions throughout the body. Humanin and MOTS-c, hormones that appear to have significant roles in metabolism and diseases of aging, are unlike most other proteins, as they are encoded in mitochondria, rather than in the cell's nucleus where most genes are contained. Aged mammals contain high quantities of oxidized lipids and proteins, as well as damaged/mutated DNA, particularly in the mitochondrial genome. A major effect of mitochondrial dysfunction is an inappropriately high generation of ROS and proton leakage, resulting in lowering of ATP production in relation to electron input from metabolism. Leaked ROS and protons cause damage to a wide range of macromolecules, including enzymes, nucleic acids and membrane lipids within and beyond mitochondria and thus are consistent with the inflammation theory of aging as being proximal events triggering the production of pro-inflammatory cytokines. Free radicals can damage the mitochondrial inner membrane, creating a positive feedback-loop for increased free-radical creation. Induction of ROS generates mtDNA mutations, in turn leading to a defective respiratory chain. Defective respiratory chain generates even more ROS and generates a vicious cycle. One aspect of the present invention is directed to a therapeutic approach that employs autophagy, and preferably mitophagy, to reduce muscle damage and wasting and to also reduce the likelihood of osteoporosis. In certain embodiments, the use of the described treatment can be employed to combat human muscular dystrophy (DMD). Autophagy is known to be defective in human muscular dystrophy and such defect contributes to the pathogenesis of the disease.

Mitochondria are the cell's chief energy producing organelles. A cell can contain hundreds of mitochondria, the DNA of which encodes a subset of mitochondrial RNA and proteins. The mitochondrial theory of aging proposes that mutations progressively accumulate within the mitochondrial DNA. The consequences are predicted to be particularly dire for non-proliferative cells in organs that have a minimal capacity to regenerate (quiescent tissues), such as the heart and brain. The activity of master regulators of mitochondrial function and number diminishes with aging, further contributing to mitochondrial deficiency. For example, with age, telomere damage in the nucleus triggers the activation of p53, which can have different effects. p53 is a gene that directs damaged cells to stop reproducing or die. The gene helps prevent cancer in younger people but may be partly responsible for aging by impairing the body's ability to renew deteriorating tissues. Prominent age-related diseases are further believed to be related to hormesis, in which biological stress, such as exercise, elicits a biological response that confers resistance to greater amounts of stress. This effect is due to increased formation of free radicals within the mitochondria causing a secondary induction of increased antioxidant defense capacity. Mitochondria are central to metabolic processes and are is involved energy production, programmed cell death, reactive oxygen species (ROS) generation, and is implicated in various stages of major diseases including cancer, diabetes, neurodegenerative diseases, and aging. In proliferative cells, p53 halts both cell growth and DNA replication, potentially causing apoptotic cell death. p53 also represses the expression of PGC-1 in mitochondria, reducing the function and number of these organelles, and so leading to age-related dysfunction of mitochondrion-rich, quiescent tissues. The mitochondrial derangements driven by loss of PGC-1 activity may independently lower the threshold for the generation of toxic intermediates such as reactive oxygen species (ROS), which damage mitochondrial DNA, thus setting up a vicious cycle of further mitochondrial dysfunction. Mitochondria-derived humanin shares 92-95% identity with several nuclear-encoded cDNAs. A 24 amino acid peptide, known as humanin (HN), is highly conserved among species (between 90-100% homology), including lower organisms. Unlike most other proteins, humanin and MOTS-c are encoded in mitochondria, the structure within cells that produces energy from food, instead of in the cell's nucleus where most genes are contained. As humanin and MOTS-c are hormones that have significant roles in metabolism and the diseases of aging, the regulation of the same via production of the same via an individual's microbiome forms one aspect of various embodiments of the present invention. Similarly, the SHLP family of compounds that are expressed by mitochondria play a major role in the intracellular signaling and communication to regulate metabolism and cell fate and thus are important in addressing methods for combating aging.

Certain embodiments of the present invention are directed to bacterial production by genetically modified bacteria to produce or to be used in conjunction with one of xylitol, tomatidine and/or rapamycin, especially the precursors thereof such that biosynthesis of these agents can be provided to those in need, e.g. those suffering from osteoporosis. Bacteria that may produce xylitol include *Corynebacterium* sp., *Enterobacterium liquefaciens*, *Serratia marcescens*, *Bacillus coagulans* and *Mycobacterium smegmatis*. Certain embodiments of the present invention involve the production of xylitol by genetically modified bacteria, including those listed above, preferably using CRISPR systems to include genes responsible for xylitol production in yeasts, such as *Pichia stipitis*. The genes of yeasts that encode for xylitol production are well known by those of skill in the art. Incorporation of these genes into suitable bacterial vectors is within the skill of those in the art. For example, deletion of the *Escherichia coli* xylulokinase gene (xylB) is essential for achieving high xylitol titers from xylitol-producing *E. coli* strains growing on glucose in the presence of xylose. The yeast *Pichia stipitis* naturally produces xylitol. Replacement of xylB with XYL3 results in drastically enhanced xylitol titers from *E. coli* strains co-expressing xylose reductase during growth on xylose. Biological conversion of xylitol using microorganisms is achieved in some embodiments via using genetically modified microorganisms capable of converting readily available carbon sources, such as D-glucose, into xylitol.

In certain embodiments, in addition to xylitol, tomatidine and/or rapamycin, the formulation includes at least one calcium source. According to a particular embodiment, the calcium source is any compound containing calcium, including salt complexes, solubilized species, and other forms of calcium. Non-limiting examples of calcium sources include amino acid chelated calcium, calcium carbonate, calcium oxide, calcium hydroxide, calcium sulfate, calcium chloride, calcium phosphate, calcium hydrogen phosphate, calcium dihydrogen phosphate, calcium citrate, calcium malate, calcium citrate malate, calcium gluconate, calcium tartrate, calcium lactate, solubilized species thereof, and combinations thereof. In still other embodiments, the formulation includes a magnesium source. The magnesium source is any compound containing magnesium, including salt complexes, solubilized species, and other forms of magnesium. Non-limiting examples of magnesium sources include magnesium chloride, magnesium citrate, magnesium gluceptate, magnesium gluconate, magnesium lactate, magnesium hydroxide, magnesium picolate, magnesium sulfate, solubilized species thereof, and mixtures thereof. In another particular embodiment, the magnesium source comprises an amino acid chelated or creatine chelated magnesium. In still other embodiments, the formulation includes one or more of vitamins D, C, K, their precursors and/or beta-carotene and combinations thereof.

Yet further embodiments include in the formulation at least one plant extract selected from the group that include species of the genus *Taraxacum* and *Amelanchier*, as disclosed in U.S. Patent Publication No. 2005/0106215, and species of the genus *Lindera*, *Artemisia*, *Acorus*, *Carthamus*, *Carum*, *Cnidium*, *Curcuma*, *Cyperus*, *Juniperus*, *Prunus*, *Iris*, *Cichorium*, *Dodonaea*, *Epimedium*, *Erigonoum*, *Soya*, *Mentha*, *Ocimum*, *thymus*, *Tanacetum*, *Plantago*, *Spearmint*, *Bixa*, *Vitis*, *Rosemarinus*, *Rhus*, and *Anethum*.

It has been observed by the present inventor that producing Haiku resembles the generation of a patent claim. There is requisite structure, a need to communicate substance and an ethereal quality of understanding. As one of skill in the art of both biology and haiku will appreciate with respect to osteoporosis:

Osteoporos
. . . is more than just a gut feeling
Tomatidine cures.

While specific embodiments and applications of the present invention have been described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. Those skilled in the art will appreciate that the conception upon which this disclosure is based, may readily be utilized as a basis for designing of other methods and systems for carrying out the several purposes of the present invention. It is important, therefore, that the claims be regarded as including any such equivalent construction insofar as they do not depart from the spirit and scope of the present invention.

What is claimed is:

1. A method for reducing the likelihood of osteoporosis in an individual human being, said method comprising: substantially reducing the human being's resident populations of gut microbes prior to administering a therapeutically effective amount of a bacterial formulation comprising *Coprococcus*; and providing fructan fiber inulin in an amount sufficient to reduce the pH in the colon of the human being to achieve acidifying of the colon, wherein the bacteria formulation includes bacteria that have been modified to increase the level of butyrate in the human being's gut by the bacterial formulation.

2. The method of claim 1, wherein the beneficial formulation is encapsulated.

3. The method of claim 1, wherein the *Coprococcus* bacteria employed are first isolated from a human being's stool and where the *Coprococcus* bacteria are from the human being treated.

4. The method of claim 1, further comprising administering tomatidine to the human being.

5. The method of claim 1, wherein the bacterial formulation comprises bacteria modified via a clustered regularly interspaced short palindromic repeats (CRISPR) CRISPR associated protein (Cas) system or a CRISPR from *Prevotella* and *Francisella* 1(Cpf1) system.

6. The method of claim 1, further comprising reducing bacteria in the gut of the human being, wherein the bacteria reduced are selected from the group consisting of *Pediococcus*, *Streptococcus*, *Enterococcus*, and *Leuconostoc* bacteria.

7. The method of claim 6, wherein the step of reducing the number of bacteria comprises administering an antibiotic.

8. The method as set forth in claim 6, further comprising reducing the number of bacteria in the human being's gut using a clustered regularly interspaced short palindromic repeats (CRISPR) CRISPR associated protein (Cas) system or a CRISPR from *Prevotella* and *Francisella* 1(Cpf1) system.

9. The method of claim 1, wherein the bacterial formulation further comprises a bacterium selected from the group consisting of *Chlamydia*, *Shigella flexneri*, *Mycoplasma* bacteria, *Lactobacillus casei*, *Roseburia*, *Bifidobacterium*, and *Faecalibacterium prausnitzii*.

10. The method of claim 1, further comprising increasing the levels of bacterial genera selected from the group consisting of *Bifidobacterium*, *Lachnospira*, *Roseburia*, *Lactobacillus* and *Shigella*.

11. A method for reducing the likelihood of developing osteoporosis in an individual, comprising: providing in the gut of an individual bacteria from a population of beneficial bacteria selected from the group consisting of *Coprococcus, Roseburia, Bifidobacterium*, and *Faecalibacterium prausnitzii*; and administering fiber to the individual to maintain a therapeutically effective amount of the beneficial bacteria in the gut of the individual; and administering to the individual at least 10 micro-mole of tomatidine.

12. The method as set forth in claim 11, further comprising, providing in the gut of the individual bacteria selected from the group consisting of *Lactobacillus* species; administering at least 6 grams per day of fiber to the individual to maintain a therapeutically effective amount of the beneficial bacteria in the gut of the individual human being; and increasing the levels of at least one of *Roseburia* and *Faecalibacterium prausnitzii* in the individual's gut microbiome.

13. The method as set forth in claim 11, further comprising reducing the number of bacteria in the human being using a clustered regularly interspaced short palindromic repeats (CRISPR) CRISPR associated protein (Cas) system or a CRISPR from *Prevotella* and *Francisella* 1(Cpf1) system.

14. The method as set forth in claim 11, further comprising increasing the levels of bacteria in the individual selected from the group consisting of *Bifidobacterium, Prevotella, Lachnospira*, and *Shigella*.

15. The method as set forth in claim 11, wherein said beneficial bacteria have been modified by using a clustered regularly interspaced short palindromic repeats (CRISPR) CRISPR associated protein (Cas) system or a CRISPR from *Prevotella* and *Francisella* 1(Cpf1) system.

16. A method for reducing the likelihood of developing osteoporosis in an individual human being, comprising: providing in the gut of an individual a population of beneficial bacteria selected from the group consisting of *Faecalibacterium prausnitzii* and/or *Akkermansia muciniphila*; administering at least 6 grams per day of fiber to the individual to maintain a therapeutically effective amount of the beneficial bacteria in the gut of the individual human being; and administering tomatidine to the individual human being.

17. The method as set forth in claim 16, further comprising administering to the individual human being a bacteria selected from the group consisting of *Streptococcus, Actinomyces, Veillonella, Fusobacterium, Porphyromonas, Prevotella, Treponema, Neisseria Haemophilus, Lactobacillus, Capnocytophaga, Eikenella, Leptotrichia, Peptostreptococcus, Propionibacterium, Chlamydia, Shigella flexneri, Mycoplasma bacteria, H. pylori*, and *Streptomyces hygroscopicus* and selectively reducing in the individual's gut microbiome bacteria selected from the group consisting of *Actinomyces*, Eggerthella, and *Clostridium* Cluster XIVa.

18. The method as set forth in claim 16, further comprising administering at least 0.1 mg of rapamycin.

19. The method of claim 16, wherein said administering of tomatidine step comprises providing the individual with a bioadhesive strip having a first and second side, the second side having a bioadhesive that is adapted to bind to a mucosal membrane for at least 1 hour while inside a person's mouth, said strip including at least one polymer selected from the group consisting of pullulan, hydroxypropylmethyl cellulose, hydroxyethyl cellulose, sodium alginate, polyethylene glycol, tragacanth gum, guar gum, acacia gum, arabic gum, carboxyvinyl polymer, amylose, high amylose starch, hydroxypropylated high amylose starch, dextrin, chitin, chitosan, levan, elsinan, collagen, zein, gluten, soy protein isolate, whey protein isolate, casein and mixtures thereof; wherein said strip includes tomatidine.

* * * * *